United States Patent [19]
Carroll

[11] Patent Number: 5,962,008
[45] Date of Patent: Oct. 5, 1999

[54] TOPICAL MEDICAMENT FOR USE IN TREATMENT OF ANORECTAL INFLAMMATION

[76] Inventor: MaryAnn Carroll, 284 Jackson St., Denver, Colo. 80206

[21] Appl. No.: 09/083,308

[22] Filed: May 22, 1998

[51] Int. Cl.[6] ..................................................... A61F 13/00
[52] U.S. Cl. ......................... 424/436; 424/434; 514/882; 514/937; 514/938; 514/930
[58] Field of Search .................................... 424/422, 434, 424/436; 514/882, 937, 938

[56] References Cited

U.S. PATENT DOCUMENTS 4,329,366  5/1982  Nashed et al. ........................... 424/324
4,797,392  1/1989  Chernomorsky ......................... 514/185
5,538,728  7/1996  Yanaki et al. ............................ 424/401

*Primary Examiner*—Thurman K. Page
*Assistant Examiner*—Lakshmi Channavajjala
*Attorney, Agent, or Firm*—Duft, Graziano & Forest, P.C.; Dan Cleveland, Jr., Esq.

[57] ABSTRACT

A medicament for use in the treatment of anorectal inflammation in hemorrhoids and the like contains a petroleum base, water, phenylephrine hydrochloride, squalene, and 8-hydroxyquinoline.

8 Claims, No Drawings

TOPICAL MEDICAMENT FOR USE IN TREATMENT OF ANORECTAL INFLAMMATION

BACKGROUND OF THE INVENTION

1. Field of the Invention

The present invention pertains to the field of topical ointments or creams that may be used to sooth pain, swelling, and itching that is associated with anorectal inflammation caused by hemorrhoids and the like. More specifically, the topical ointment contains a vasoconstrictor in combination with a plurality of antibacterial agents.

2. Statement of the Problem

Discomfort due to anorectal inflammation includes pain and itching in tissues proximate the rectum. Anorectal inflammation is most often found in irritated hemorrhoidal tissues, i.e., hemorrhoids, which are varicose dilations of veins in the superior or inferior hemorrhoidal plexus. The dilation results from a persistent increase in venous pressure. Inflammation of anorectal tissues is a complicating factor that enhances the severity of hemorrhoids. The patient often suffers from chronic pain and itching. The inflamed tissue becomes sensitized to the application of medicines intended to treat the problem, and this sensitization can actually cause the medicines to worsen the problem that they are intended to treat. Over time, surgery may be required to remove hemorrhoidal tissues; however, even surgery sometimes does not eliminate the continuing tendency of these tissues to become inflamed. In fact, surgery is only a temporary solution to the problem in most instances. Thus, the cycle of inflammation, discomfort, and sensitization repeats itself even after surgery.

Surgical ligation of hemorrhoids is complicated by the risk of infection, and exotic procedures have been developed, e.g., as described in U.S. Pat. No. 4,621,635, which teaches rubber band ligation of internal hemorrhoidal tissue, followed by a laser incision around the perimeter of the base of the external hemorrhoid portions. The surface of the external hemorrhoid is then evaporated with a traversing movement of the laser beam. The laser beam is then employed to form a cavity into the core of the hemorrhoid and dimensioned to accommodate the subsequent insertion of a cryogenic probe. The probe freezes the hemorrhoidal tissue from the interior outwardly.

There are many different categories of hemorrhoids or hemorrhoidal conditions, and some of these are medically severe conditions requiring surgery. External hemorrhoids result from a varicose dilation of a vein of the inferior hemorrhoidal plexus situated distal to the pectinate line. External hemorrhoids are typically covered with modified anal skin. Internal hemorrhoids are formed of a varicose dilation of the superior hemorrhoidal plexus originating above the pectinate line and covered by mucous membrane. Mucotaneous hemorrhoids result from a varicose dilation of a vein connecting the superior and inferior hemorrhoidal plexuses with the formation of internal and external hemorrhoids in continuity. Prolapsed hemorrhoids are internal hemorrhoids that have descended below the pectinate line with protrusion outside the anal sphincter. Strangulated hemorrhoids are prolapsed hemorrhoids that are sufficiently sever for the action of the anal sphincter to have occluded the blood supply. Thrombosed hemorrhoids contain clotted blood.

The majority of hemorrhoidal conditions are not so severe as to require surgery. Hemorrhoids and associated discomfort due to anorectal inflammation can be treated through the use of topical ointments. Most recent U.S. patents directed towards hemorrhoids and anorectal inflammation pertain to complicated dispensing apparatus for medicinal preparations. U.S. Pat. No. 4,938,221 relates to a hemorrhoid inflammation reducing device having a hollow flexible housing that is shaped to be inserted into and removed from the anus of the rectum of a person having internal or external hemorrhoids. A coolant is disposed within the housing for shrinking the internal/external hemorrhoids. A closure is provided for sealing the coolant within the housing after the coolant is placed within the housing. U.S. Pat. No. 5,004,636 relaters to a roll-type toilet tissue that is formed in three layers, with one layer having a hemorrhoid-treating medication sandwiched between the two other layers. U.S. Pat. No. 4,906,239 relates to a hemorrhoid-treatment rod that is shaped like a cone in order to dilate the anus. Ointment is forced into the cone for dispensation onto the anus, and the ointment can be massaged into the area to be treating by rotating the rod without being wiped off prematurely.

A widely used topical ointment for the treatment of hemorrhoids is PREPARATION H® (a trademark of Whitehall-Robbins Healthcare located in Madison, N. J.). PREPARATION HO contains active ingredients including 71.9% petrolatum, 14% mineral oil, 3% shark liver oil, and 0.25% phenylephrine HCl. Other ingredients include beeswax, benzoic acid, BHA, corn oil, glycerin, lanolin, lanolin alcohol, methylparaben, parrafin, propylparaben, thyme oil, tocopherol, and water. The phenylephrine HCI is a vasoconstrictor that is used to shrink the venous dilations which are the underlying cause of hemorrhoids. Many patients have reported that even vasoconstricting products, such as PREPARATION H®, do not provide complete relief from the anorectal inflammation accompanying hemorrhoids.

There remains a true need for a medicament that provides enhanced relief to patients suffering form anorectal inflammation, such as the anorectal inflammation that is often associated with hemorrhoids.

SOLUTION

The present invention overcomes the problems outlined above by providing enhanced relief to patients suffering form anorectal inflammation. This enhanced relief is obtained by using an ointment including a vasoconstrictor in combination with a penetrant-carrier of lipid soluble materials and non-sensitizing lipid-soluble antimicrobial agents. In combination, these ingredients simultaneously address the problems of venous pressure-swelling and chronic inflammation in anorectal tissues. The non-sensitizing antimicrobial active agent is effective even on patients that have been sensitized to other over-the counter medicaments. The non-sensitizing antimicrobial agent has the added benefit of suppressing odors, which is of psychological importance to many persons who use over-the-counter hemorrhoid ointments. Other distinct advantages of the preferred formulation include a relatively high melting point in excess of 100 F. to 130 F. to prevent melting of the ointment from body heat, a slightly acidic pH, and a thickness suitable for use as a protective barrier over inflamed anorectal tissues.

A topical ointment according to the invention contains a petroleum base, water, a water-soluble vasoconstrictor, and an emulsifier in an effective amount for preventing separation of the petroleum base and the water. In combination with the foregoing ingredients, the ointment contains a carrier for lipid-soluble materials and a non-sensitizing lipid-soluble antimicrobial agent.

The preferred ointment has a consistency provided by the petroleum base consisting of petrolatum in an amount less than sixty percent by weight of the ointment and the water comprising less than twenty percent by weight of the ointment. The most preferred vasoconstrictor is phenylephrine hydrochloride in an amount up to 0.3 percent by weight of the ointment. The carrier is preferably a surface-active agent, and squalene is particularly preferred. The non-sensitizing lipid-soluble antimicrobial agent is most preferably 8-hydroxyquinoline. The use of squalene in combination with 8-hydroxyquinoline and a vasoconstrictor are critical aspects of preferred embodiments of the invention that provide superior treatment results in human patients.

The ointment or cream is used by topical application to inflamed anorectal tissues. The patient usually experiences immediate soothing of pain and itching.

Inflamed hemorrhoidal tissues are observed to shrink in a matter of hours, and the ointment has been used successfully to treat inflamed hemorrhoids where commercially available ointments intended for this purpose have failed.

DETAILED DESCRIPTION OF THE PREFERRED EMBODIMENT

A general concept of the present invention pertains to the use of a medicament for use in the treatment of anorectal inflammation wherein the medicament includes a vasoconstrictor in combination with one or more antimicrobial agents and a carrier-penetrant for the antimicrobial agent. Action of the antimicrobial agent is facilitated by use of the carrier-penetrant.

A preferred feature of the invention is that all of the ingredients used to make the ointment have been approved for over-the-counter use, especially for use as cosmetic chemicals. The U.S. Food and Drug Administration has approved guidelines for the use of cosmetic chemicals that are commonly provided in over-the-counter ointments. These chemicals are submitted to the FDA for over the counter drug review and approval. Approval is indicated by a final publication or report in the form of a monograph. The *Cosmetic Ingredient Review, Ingredient Publication Status* (Jun. 24, 1994) from the Cosmetic & Toiletry Foundation Association in Washington, D.C. provides a list of approved cosmetic chemicals. This publication provides a list of approved cosmetic ingredients, the approved functions for these ingredients, and citations to the corresponding monograph publications for each ingredient. These "cosmetic" ingredients can be used in topical ointment, as well as other products such as lotion, hair dye and the like. The general nature and function is known for each ingredient, but great variations in efficacy can be observed based upon the precise selection of ingredients and the concentration of ingredients in combination.

An emulsified petroleum base is used as a vehicle for the ointment. The petroleum base is preferably a high grade of petrolatum, such as snow white petrolatum. Petrolatum is preferred for its effects in soothing the sensations of burning, itching and pain that are experienced by those who are suffering from anorectal inflammation. Mineral oil may be used to thin the consistency of the ointment. The petroleum base preferably ranges from thirty to seventy percent by weight of the ointment, is more preferably from forty to sixty percent, and is most preferably fifty percent of the ointment by weight. Non-petroleum waxes e.g., beeswax, may also be added to thicken and facilitate emulsion of the base. For example, a preferred formulation contains beeswax in an amount ranging from 7.0 to 7.5 percent of the ointment weight, in order to stabilize the emulsion.

The use of a petrolatum base in amounts less than about fifty or sixty percent of the ointment or cream by weight is significant because these amounts reflect a reduction in the amount of petrolatum that is used in comparison with other over-the-counter remedies including PREPARATION H®. Users of these other ointments sometimes complain that the ointment melts and runs away from the rectal area with the effect of staining the clothes of the person who wears the ointment. The reduced weight of petrolatum in the present medicament is associated with a corresponding reduction in the effect of staining clothes if the ointment does melt; however, the ointment resists melting because it has a higher meting temperature than other ointments intended for this purpose.

Purified water is also used to form a portion of the ointment or cream base. The water solubilizes ingredients that are not soluble in the petroleum portion of the base. The amount of water preferably ranges from forty to ten percent by weight of the ointment. Preferably, no more water is added than is necessary to solubilize the water soluble ingredients of the ointment. It is intended that the water will form a stable emulsion with the petroleum base and, consequently, water in amounts exceeding a 1:2.5 weight ratio of water to petrolatum may require homogenation of the mixture or the addition of a water soluble polymer, such as a biocompatible cross linked polyacrylate polymer.

An emulsifier is used to stabilize the emulsion and provide a melting point in excess of about 100° F. to 130° F. A plurality of emulsifying agents are preferably used as the emulsifier. These emulsifying agents can include, by way of example, squalene, sodium borate, lanolin alcohol, and sorbitan sesquioleate, as well as other conventional emulsifiers approved for cosmetic use. The emulsifiers are added in amounts that, in combination, stabilize the petroleum and water emulsion. The combined amount of emulsifier typically ranges from three to ten percent of the ointment by weight. Many of these emulsifiers have dual or triple purposes. For example, squalene functions as a surfactant and penetrant while providing a nutritional benefit to inflamed tissues.

Lanolin doubles as an emollient. Emollients are also present in preferred formulations with lanolin being the most preferred emollient. Glycerine or another humectant may added to alternative formulations in the semisolid suppository form. In combination, the emollient and humectant portions of the ointment preferably range from sixteen to seventeen percent by weight of the ointment.

Phenylephrine hydrochloride is a vasoconstrictor that has been approved for over-the-counter use in amounts not exceeding about 0.3 of the composition weight. Phenylephrine hydrochloride is water-soluble, and preferably present in an amount equal to a 0.013:1 weight ratio of phenylephrine hydrochloride to water, not to exceed about 0.25 weight percent of phenylephrine hydrochloride in the ointment. Other vasoconstrictors may be use in the invention, but phenylephrine hydrochloride is preferred because it has been approved for use in over-the-counter ointments. The phenylephrine hydrochloride is preferably mixed with the water prior to adding the water to the petrolatum.

Low sensitizing preservatives are useful for enhancing the shelf storage life of the ointment. It is preferred to avoid the use of chlorides as preservatives because chlorides can sometimes promote severe sensitization reactions in patients with side effects that include enhanced inflammation, ulceration, and bleeding. Suitable low sensitizing preservatives include the parabens (methyl and propyl parabens), as well as EDTA, such as trisoidium EDTA. Tocopherol acetate is also useful as a preservative, ands has the addition benefit of providing nutritional benefit to inflamed anorectal tissues in the form of a vitamin E derivative.

Especially preferred forms of the invention include the use of methyl salicylate as a fragrance in an amount up to 0.3 percent of the ointment by weight. Methyl salicylate has the addition benefit of being a counterirritant with soothing effects on inflamed anorectal tissues.

The non-sensitizing antimicrobial agent is preferably a lipid soluble material. A particularly preferred cosmetic biocide for use in the present invention as an antimicrobial agent is 8-hydroxyquinoline. Oxyquinolines have a broad spectrum of antimicrobial activity in combination with a low incidence of sensitivity reactions in sensitized patients who suffer from chronic inflammation. The antimicrobial agent is preferably not a chloride because chlorides are likely to induced sensitivity reactions that sometimes can produce eshcarotic effects. The use of oxyquinoline is further preferred for the effect of providing a slightly acidic pH to the overall ointment or cream. The acidic pH promotes healing of inflamed anorectal tissues, As indicated above, squalene (2,6,10,15,1 9,23-hexamethyl-2,6,10,14,18,22-tet racosahexene) is optionally used as an emulsifier. Squalene is also a surfactant, a carrier for lipid soluble materials, a mild antimicrobial agent, and a substance that provides nutritional benefit to inflamed anorectal tissues. The surfactant effects of squalene are synergistic in combination with lipid soluble antimicrobial agents, such as oxyquinoline, because squalene enhances the ability of lipid soluble materials to penetrate the skin. A further synergism that occurs in mixtures of vitamin E, squalene, and oxyquinoline is the ability to inhibit microbial growth while enhancing cell renewal through nutritional and enzymatic bioaction. In particular, squalene enhances the ability of oxyquinoline to penetrate inflamed anorectal tissues for accelerated antimicrobial action. Squalene also facilitates the delivery of nutritionally beneficial lipid soluble materials including vitamin E, as well as lipid soluble anti-inflammatory agents and counterirritants. A variety of soaps or other surfactants could also be used with the effect of being a carrier-penetrant for lipid soluble materials; however, squalene is particularly preferred for the substantial absence of sensitization reactions in patients having inflamed anorectal tissues.

The following non-limiting examples are used to present the most preferred product formulation, as well as evidence of biological utility of this formulation in actual use on human patients.

EXAMPLE 1

A TOPICAL OINTMENT FOR USE IN THE TREAMENT OF ANORECTAL INFLAMMATION

The following ingredients were weighed out and blended to substantial homogeneity in a stable emulsion to form a medicinal cream. This formulation is particularly preferred for its ability to adhere to inflamed anorectal tissues while providing multiple benefits to the tissues according to the principles discussed above.

TABLE 1

INGREDIENTS

| Ingredient | Weight Percent | Purpose |
| --- | --- | --- |
| Snow White Petrolatum | 50 | Active agent for soothing and protection of inflamed tissues; mild desiccant |
| Phelylephrine hydrochloride | 0.25 | Active ingredient vasoconstrictor |
| Purified water | 19 | Solubilizing agent for Phenylephrine hydrochloride; thinner for emulsified base |
| Lanolin | 16.5 | Emulsifier |
| Beeswax | 7.5 | Emulsifier, thickening agent |
| Squalene | 2.5 | Emulsifier, bactericide, carrier of lipid-soluble materials, surface active agent, penetrant |
| Tocopherol acetate | 1 | Preservative, vitamin E nutritional benefit |
| Sodium borate | 0.94 | Emulsifier |
| Lanolin alcohol | 0.5 | Emulsifier |
| Methyl salicylate | 0.25 | Fragrance, counterirritant |
| Sorbitan sesquioleate | 0.25 | Emulsifier |
| 8-hydroxyquinoline | 0.22 | Odor neutralizer, antimicrobial agent |
| Methylparaben | 0.25 | Preservative |
| Propylparaben | 0.1 | Preservative |
| Trisodium EDTA | 0.05 | Preservative |

EXAMPLE 2

USE OF THE OINTMENT ON HUMANS

Aliquots of the ointment from Example 1 were given to thirty people who suffer from inflammation of hemorrhoids, These people all had a history of using over-the-counter ointments or creams, and had at the time of the test all of these persons had experience with commercially available products. Twenty nine of these people reported that the ointment of Example 1 provided greater symptom relief than they had been able to obtain with any other over the counter hemorrhoid product. One person reported that the ointment of example 1 provided equal relief in comparison to another medication.

A board certified member of the American Osteopathic Association wrote the following evaluation of the Example 1 cream:

I'm writing to give you my impression of your new hemorrhoid preparation. I have used it periodically for the last three months with great results. My condition settled down and the discomforts were quickly controlled. To satisfy my own curiosity I used a prescription medication for a week during a flare up and found it's affects comparable to those of your preparation. In comparison to other over the counter preparations I have used in the past yours does not have an objectionable odor and does not stain undergarments. All in all I was quite impressed with it. I believe it is superior to other OTC preparations available and comparable to the prescription preparations currently available.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

I claim:

1. A topical medicament for use in the treatment of anorectal inflammation, consisting of:
   a petroleum base;
   water;
   phzenylephrine hydrochloride;
   an emulsifier in effective amounts for preventing separation of said petroleum base and said water;
   a carrier for lipid-soluble materials;
   oxyquinoline; and
   a compatible material selected from the group consisting of tocopherol acetate methyl salicylate, parabens, EDTA, and combinations thereof.

2. The medicament as set forth in claim 1 wherein said petroleum base consists of petrolatum in an amount less than sixty percent by weight of the ointment.

3. The medicament as set forth in claim 2 wherein said phenylephrine hydrochloride is present in an amount up to 0.3 percent by weight of the ointment.

4. The medicament as set forth in claim 3 wherein said water consists of less than twenty percent by weight of the ointment.

5. The medicament as set forth in claim 1 wherein said carrier is a surface-active agent.

6. The medicament as set forth in claim 5 wherein said carrier is squalene.

7. The medicament as set forth in claim 1 wherein said compatible material is methyl salicylate.

8. A method for treating inflammation in anorectal tissues, said method comprising the steps of:
   obtaining a medicament consisting of a petroleum base, water, phenyiephrine hydrochloride, an emulsifier in effective amounts for preventing separation of said petroleum base and said water, a carrier for lipid-soluble materials, oxyquinoline; and a compatible material selected from the group consisting of tocopherol acetate methyl salicylate, parabens, EDTA, and combinations thereof,
   applying said medicament to inflamed anorectal tissues; and
   permitting said medicament to reduce symptoms of inflammation in said anorectal tissues.

* * * * *